US006720766B2

(12) United States Patent
Parker et al.

(10) Patent No.: US 6,720,766 B2
(45) Date of Patent: Apr. 13, 2004

(54) THIN FILM PHANTOMS AND PHANTOM SYSTEMS

(76) Inventors: Kevin J. Parker, 166 Superior Rd., Rochester, NY (US) 14625; Daniel B. Phillips, 1720 Mt. Hope Ave., Rochester, NY (US) 14620

( * ) Notice: Subject to any disclaimer, the term of this patent is extended or adjusted under 35 U.S.C. 154(b) by 0 days.

(21) Appl. No.: 10/345,988

(22) Filed: Jan. 17, 2003

(65) Prior Publication Data

US 2003/0122544 A1 Jul. 3, 2003

Related U.S. Application Data

(63) Continuation of application No. 08/807,019, filed on Feb. 26, 1997, now abandoned, which is a continuation-in-part of application No. 08/423,328, filed on Apr. 14, 1995, now Pat. No. 5,756,875.

(51) Int. Cl.[7] .................................................. G01V 3/00
(52) U.S. Cl. ........................................ 324/308; 378/207
(58) Field of Search ................................. 324/308, 300, 324/306, 307, 309, 312, 314, 318, 322; 600/420, 421, 426; 378/207, 18

(56) References Cited

U.S. PATENT DOCUMENTS

| | | | | |
|---|---|---|---|---|
| 4,280,047 A | * | 7/1981 | Enos | 250/252.1 |
| 4,794,631 A | * | 12/1988 | Ridge | 378/207 |
| 5,036,280 A | | 7/1991 | Chesavage | 324/308 |
| 5,756,875 A | | 5/1998 | Parker et al. | 73/1 DV |
| 5,994,900 A | * | 11/1999 | Gurvich | 324/300 |
| 6,315,447 B1 | * | 11/2001 | Nord et al. | 378/207 |

* cited by examiner

Primary Examiner—Louis Arana
(74) Attorney, Agent, or Firm—Blank Rome, LLP

(57) ABSTRACT

Phantoms for testing and measuring the performance of magnetic resonance imaging (MRI) and x-ray computed tomography (CT) imaging systems have regions of precisely controlled magnetic resonance and x-ray absorption imaging properties. These regions contain subresolvable regions, or distinct micro regions, with pre-selected magnetic resonance or x-ray absorption properties, called scatterers. The regions are precisely positioned so as to define patterns which form images from which the performance of the imaging system can be evaluated to assure the quality of the images. The phantoms can reveal the combined influences of all the stages in the imaging chain in terms of modulation transfer function and resolution limits as well as other artifacts and defects in the system such as aliasing and degraded spatial frequency response which cannot be evaluated with conventional phantoms. The subresolution scattering regions may be formed by printing them on a thin film sheet or substrate using photo lithography, electrostatic xerographic printing or etching; the toner particles or deposited material forming the scatterers being sub-resolvable in size. Half-tone masks, such as blue noise masks, may be used to produce regions of precisely controlled sub-resolvable scatterers to be used for grey scale evaluation of the imaging system by producing images of different image density. The thin film sheets are thinner than the thickness of the x-ray CT beam or the MRI slice thickness excitation. The thin film sheets may be displaced, as by being vibrated. The sheets may be made of piezoelectric material having electrodes across which varying electrical signals are applied to displace the sheets thereby simulating movement of objects for Doppler measurements. Similar phantoms are used for testing and measuring the performance of ultrasonic imaging systems.

62 Claims, 16 Drawing Sheets

THIN FILM PHANTOMS AND PHANTOM SYSTEMS

REFERENCE TO RELATED APPLICATIONS

This application is a continuation of U.S. patent application Ser. No. 08/807,019, filed Feb. 26, 1997, now abandoned, which is a continuation-in-part of our application Ser. No. 08/423,328, filed Apr. 14, 1995, now U.S. Pat. No. 5,756,875, and extends the invention of that application to the field of x-ray (CT) and magnetic resonance imaging (MRI).

FIELD OF THE INVENTION

The present invention relates to systems (methods and apparatus) for testing and measuring the performance of CT & MRI imaging systems, and to test targets for CT and MRI imaging, which are often called phantoms, and enable the assessment of the performance of the imaging system in terms of criteria that modern imaging science has recognized as necessary or desirable for such assessment including, for example, the modulation transfer function of the system, resolution, aliasing, and spatial frequency response.

DESCRIPTION OF RELATED ART

CT imaging systems generate and scan x-ray beams while MRI systems obtain image information from a preselected tomographic slice or cross section of thickness typically greater than one mm. Sometimes the image signals are transmitted over communications links to a receiving station far removed from the patient where diagnoses based upon the images are made. It is important for medical imaging that the quality of the entire system be assessed. It therefore is desirable to have test targets or phantoms which provide images from which the performance of the entire system can be assessed.

Imaging science has developed criteria, such as the modulation transfer function (MTF), which can provide assessment of aliasing, spatial frequency response, and resolution limits for the evaluation of imaging systems generally. Such assessments have not been feasible with many conventional phantoms. These phantoms use objects which mimic lesions of different size and contrast. Rods, spheres, cones and other geometrical objects of a size which can be resolved by the system are used in conventional phantoms and are located in volumes containing water or tissue mimicking material (such as gels). None of these phantoms are able to produce detailed, high resolution patterns at varying contrast levels that permit accurate evaluation of MTF and other imaging science criteria which represent the performance of the imaging system. Some phantoms have been suggested which use solid bars in three-dimensional space, but these phantoms have not been provided with precisely defined patterns from which imaging science criteria can be determined.

SUMMARY OF THE INVENTION

The present invention provides a system (method and apparatus) for evaluation and assessment of MRI and CT imaging systems and improved phantoms which can test the overall response and performance of the imaging system thereby revealing system performance with imaging science criteria, such as MTF and similar analytical assessments. The combined influence of all stages in the imaging system including any communication link, which is used for teleradiography, may thereby be evaluated. Further information concerning imaging science criteria may be had from C. R. Hill et al, Ultrasound in Mod. & Biol. 17, 6, 559, and A. Rose et al, Physics Today, September 1989, P.24–32.

Phantoms can be provided in accordance with the invention on thin films or sheets by conventional printing techniques, such as electrostatic or xerographic printing, as with a laser printer, thereby providing regions with precise control in local concentration, as well as distribution, of scatterers. These are regions of sub-resolvable size (microregions) with preselected magnetic resonance or x-ray absorption properties. The scatterers are of sub-resolvable size which is less than the resolution voxel (a three-dimensional volume element-viz. a 3-D pixel). Because of the thin substrate, in the form of a planar medium on which the regions are located, tomographic imaging of the entire pattern is facilitated. The image brightness and contrast can be precisely controlled in the formation of the regions thereby providing precisely controlled MRI and CT signals, both from the regions and their positions on the substrate (the patterns of the regions). Since the actual scatterers are sub-resolvable, the imaging system can only detect their aggregate presence or absence, not the exact number and exact position of individual scatterers. The individual scatterers may be referred to as "digital" (either on or off, there or not there) in nature. The precise placement of these digital scatterers can then be used to create regions of controllable MRI or CT signal strength based on their number per unit area and their arrangement relative to each other, similar in concept to a half-tone printing process. These patterns of regions can be analyzed with the same computer system algorithms as used in conventional optics imaging systems, thus, facilitating the measurement of the imaging science criteria, such as the Modulation Transfer Function (MTF) which is defined as the normalized ratio of the measured intensity modulation of an image relative to the known intensity modulation of the originating object as a function of spatial frequency. Intensity modulation is defined as the ratio of maximum intensity difference to the sum of the intensity level extremes Imax & Imin, i.e. Modulation=

$$\frac{I\max - I\min}{I\max + I\max}$$

We have discovered that the aforementioned thin film phantom with subresolvable, digital scatterers, can also be employed to produce useful imaging science test patters for magnetic resonance imaging (MRI) and x-ray computed tomography (CT) systems. In MRI, cross-sectional images are produced whereby the image intensity depends on a number of factors including the local material magnetic properties, proton density, and relaxation constants $T_1$ and $T_2$ (See, Foundations of Medical Imaging, Cho, Jones and Singh, Wiley & Sons, NY 1993). Phantoms have been constructed using various plates, tubes, and regions that are filled with paramagnetic materials or simply materials with different proton density and relaxation constants in order to produce test patterns in an MRI image (See, U.S. Pat. Nos. 4,692,704, J. Grey, September 1987; 4,625,168, Meyer et. al, November 1986.) In CT imaging, image brightness is dependent on a number of factors including the x-ray attenuation coefficient of the materials within the imaging cross-section. CT phantoms have been constructed using various plates, tubes, and regions that possess different x-ray absorption coefficients so as to produce a pattern on the CT cross-sectional image.

The invention provides a thin-film phantom with digital scatterers in predetermined patterns. Such patterns may take the form of half-tone masks for grey scale contrast evaluation. They may be in the form of chirp and other suitable patterns for MTF and other system response criteria determination.

While electrostatic or xerographic printing is presently preferred, other techniques for making patterns on thin-film substrates including lithography, sputtering, vacuum deposition and etching may be used. The scatterers in the region are of dimensions much finer than that of a resolution voxel produced by the MRI and CT imaging system. For example, for a diagnostic MRI system using a 1.5 Tesla magnet and body coils, a 1 mm×1 mm by 3 mm slice thickness is a type of resolution voxel. A conventional 300 dots per inch laser printer using 10 micron toner particles can produce scatterers having a size of approximately 85 microns which are sub-resolvable in terms of the imaging system resolution. Thus, patterns of regions of sub-resolvable scatterers can be provided on a thin film substrate to afford phantoms for testing for different criteria. The patterns may be regularized or periodic profiles. Bars generated by a half-tones screen or mask, preferably a blue noise mask may be used. See Parker et al, U.S. Pat. No. 5,111,310 issued May 5, 1992 for information concerning blue noise mask generation by computer techniques.

As in the case of ultrasound phantoms of the parent application referenced above, the thin-film phantoms may be precisely displaced, preferably by utilizing a piezo electric material, such as PVDF as the substrate, across which a varying electrical field is applied by means of electrodes. The field may be sinusoidal to set up sinusoidal vibrations or may use other waveforms for other displacement characteristics which may be desired. For example, electrical waveforms such as ramps, chirps, AM signals, FM signals and even musical tones may be applied to induce displacements and produce Doppler signals in the audio range. The displacements are preferably at a vibration rate which should be less than the pulse repetition rate (PRF) of the pulses which comprise the interrogating beam and a size which maintains the sub-resolution characteristics of the scatterers in the regions.

Briefly described therefore, the invention provides a system for testing MRI and CT imaging systems which scan using electromagnetic energy and x-ray beams. The scan is over a plane to form an image of (para) magnetic or energy-absorbing objects in the plane. In accordance with the invention, different patterns of regions of sub-resolvable scatterers on planar mediums are provided. The mediums are of such magnetic resonance or x-ray absorption characteristics that scanning occurs in and along the plane of the medium without resonance or absorption effects. The image formed by the interaction with the pattern is analyzed to evaluate the performance of the system, preferably utilizing imaging science criteria.

BRIEF DESCRIPTION OF THE DRAWINGS

The foregoing and other features, objects and advantages of the invention as well as presently preferred embodiments thereof will become more apparent from a reading of the following description in connection with the accompanying drawings in which.

DETAILED DESCRIPTION OF THE PREFERRED EMBODIMENTS

Figure 1:
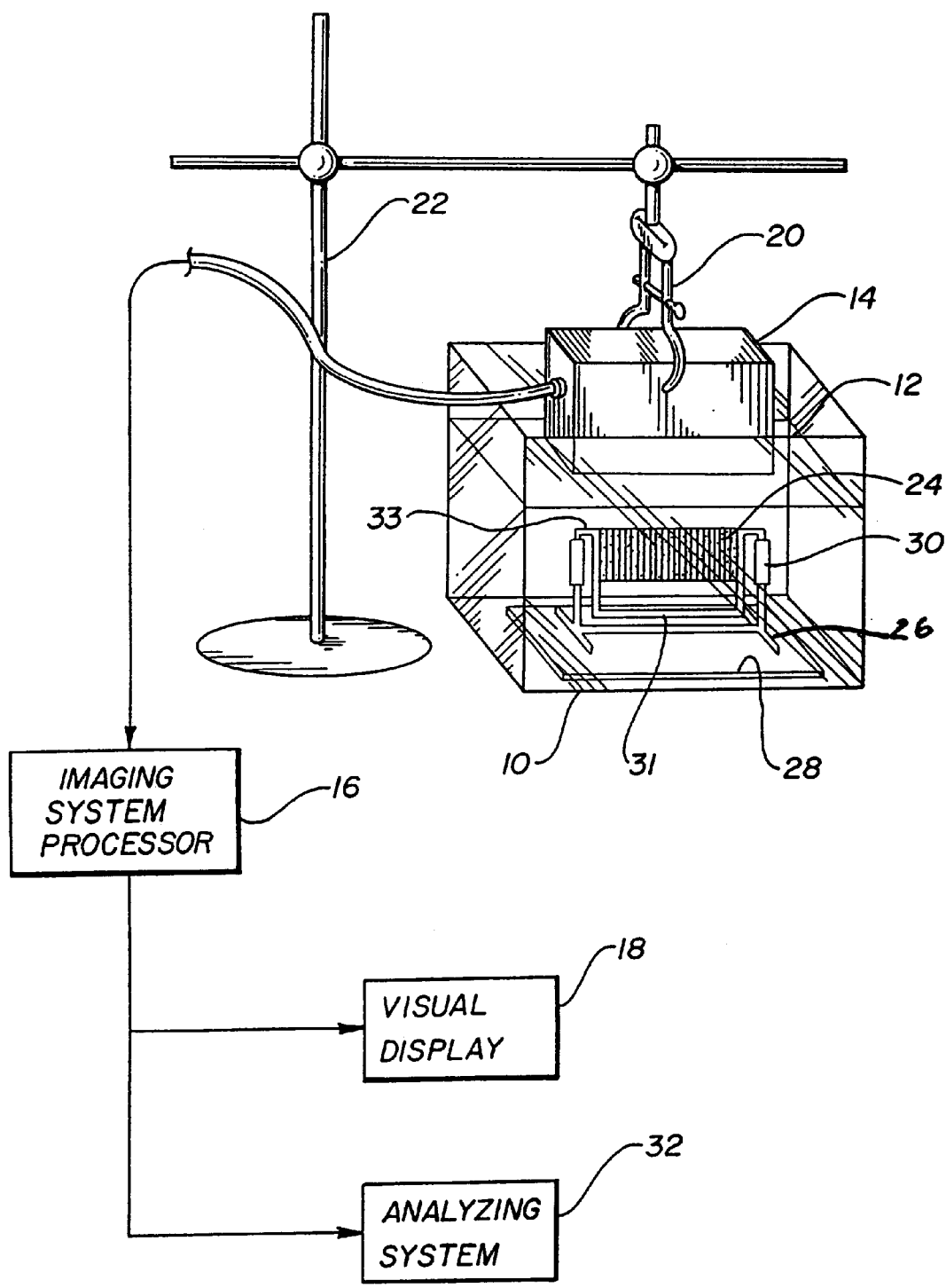
FIG. 1 is a perspective view schematically illustrating the apparatus of an ultrasonic testing system incorporating the invention.

First, consider the system of the invention as applied to the testing of ultrasonic imaging systems. Referring to FIG. 1, there is shown a tank 10 which is filled with a tissue mimicking fluid, gel or medium to a fluid level line 12 which is in the plane of the surface of the medium in the tank 10. In one case, the medium used was water. A medical ultrasound imaging system, which may be of the commercially available type includes an ultrasound transducer 14 and an imaging system processor 16 and a visual display 18. The transducer transmits and receives the ultrasonic beam and is held adjustably by a clamp 20 on a stanchion which is provided by a ring stand 22. The ring stand and clamp are adjustable universally and locate the transducer so that the ultrasonic beam projects into and scans a plane from left to right as shown in FIG. 1. The bottom surface of the transducer is at and in the plane of the water line 12, much in the same way as its transducer would be located on the surface of the skin of the patient during ultrasonic scanning operation.

The beam scanning plane is arranged by adjusting the position of the transducer so that it is coincident with the plane in which a thin film phantom 24 is located. The beam has a width or thickness in which the phantom 24 lies; preferably generally centrally located within the thickness of the beam. The phantom 24 is mounted in a U-shaped frame 33 so that it is maintained rigidly. The frame may be attached to a support bracket 26 which is seated on a plate of sound absorbing material 28 on the bottom of the tank 10. A frame clip 30 may be used to replaceably attach the phantom 24 to the bracket. This facilitates changing phantoms having different target patterns in the testing system.

The testing system also includes an analyzing system 32 which analyzes the video signal which is provided by the imaging system processor to the display 18. The analyzing signal may be of the type which is used to obtain measurements of imaging science criteria such as MTF, spatial frequency resolution, etc. Then the testing system operates in a real time on-line basis. Real time operation can also be provided where the analyzing system 32 has a camera or video frame grabber or digital compression (DICOM) data acquisition system, which obtains the image of the pattern provided by the phantom 24 for analysis by the analyzing system. Alternatively, the analyzing system may be operated off-line and derive information from analysis via a camera input which obtains video information from a photograph of the display obtained by the ultrasonic scanner under test or via a recorded video tape of the same. Alternatively, the analyzing system 32 may be an experienced human observer assessing a predetermined test pattern image for the limits of resolvability of lines, characters, or other echogenic regions formed into image science test patterns. The image for analysis may be data in memory of the processor 16 which is accessed by the analyzing system 32.

The thin-film material of the phantom which provides the insonated material has acoustic impedance close to that of the propagating medium approximates the acoustic impedance of human tissue of which ultrasonic images are made in medical ultrasound operation. Since the thin film or substrate on which the pattern providing the phantom 24 is deposited has an acoustic impedance relatively close to that of the propagating medium, in the tank 10, it should not be visualized on the display 18. The material forming the thin film pattern has a detectably different acoustic impedance than either the substrate of the phantom or the propagating medium. The pattern shown in FIG. 1 is a plurality of side-by-side vertical lines, and is only one pattern of many which may be used. The pattern selected depends upon the imaging science criteria to be analyzed. The pattern generally is a 2D pattern (2-dimensional) in the scanning plane of the beam from the transducer 14.

Generally, the pattern is made by thin film deposition techniques which provide known and even thicknesses of material on the substrate. The substrate itself is preferably of known and constant dimensions. The patterns may be deposited of uniform consistency or in the layers so as to have different consistency.

The particles contained in the pattern are sub-resolvable at the wavelength of the ultrasonic energy. The regions containing the patterns are resolvable. Since the actual scatterers are sub-resolvable, the ultrasound system can only detect their presence or absence, not any variability of the exact number and exact position of individual scatterers. The individual scatterers may be referred to as "digital" (either on or off, there or not there) in nature. The precise placement of these digital scatterers can then be used to create regions of controllable echogenicity based on their number per unit area and their arrangement relative to each other, similar in concept to a half-tone printing process. The scattering effectively determines the echogenicity of the regions. The intensity of the reflected energy depends upon the scattering strength which is precisely controlled by the pattern deposition techniques. Half-tone techniques may be used for the purpose of providing a scattering analog of the visual grey scale on the display 18.

By way of example of subresolution scatterers, for a diagnostic medical scanner with a 5 MHz transducer in soft tissue, one wavelength corresponds to approximately 300 microns. One micron features can easily be produced with conventional semi-conductor manufacturing techniques. A generally commercially available 300 dpi (dots per inch) laser printer may be used to print the regions of subresolution scatterers using 10 micron toner particles. The subresolution scatterers produced with such particles may be approximately 85 microns (i.e. dots or features) having maximum diameter of about 85 microns. Such features are sub-resolvable in terms of the wavelength of the ultrasound beam. Thus, in this example even a low cost 300 dpi laser printer can produce sufficiently high resolutions scattering patterns for the purpose of ultrasonic image system evaluation in accordance with the invention.

The pattern may be printed via laser printing on transparencies of acrylic material or Mylar (terylene, plastic) sheets. The patterns may be printed on paper, such as common 20 lb. copier bond paper and transferred to the transparency material, utilizing conventional copier duplicator systems such as the Kodak Ektaprint model 225 printer. Thus, printing directly on the substrate (transparency material) of the phantom 24 with the laser printer or indirectly by transfer to the transparency material may be used.

In one example which is presented here solely for purposes of example, the transparency material was a sheet approximately 7.6 cm. by 12.7 cm. with patterns ranging from 3.8 $cm^2$ to 6.4 cm by 7.6 cm in size. The sheet was placed inside the tank 10. These patterns were placed using the frame shown in FIG. 1 which had a rim 31 which was approximately U-shaped. The frame was made of acrylic and provided a rigidifying support for the phantom 24 as it was imaged. The substrate had a nominal measured thickness of 132 microns. The thickness of the phantom with a pattern was approximately 142 microns, the pattern being approximately 10 microns thick. The edges 33 of the transparency parallel to the face of the transducer 14, from which the beam emanated, was roughened with abrasive material (emery cloth) or cut at random angles, so as to minimize specular reflections and reverberation artifacts from this edge surface.

In this example, the image was captured and stored in the memory of a 386 DX based PC computer equipped with a video acquisition board and video analysis software which provided the analyzing system 32. Also the image was in one test was recorded on video tape and then provided to the PC for analysis.

Figure 2:
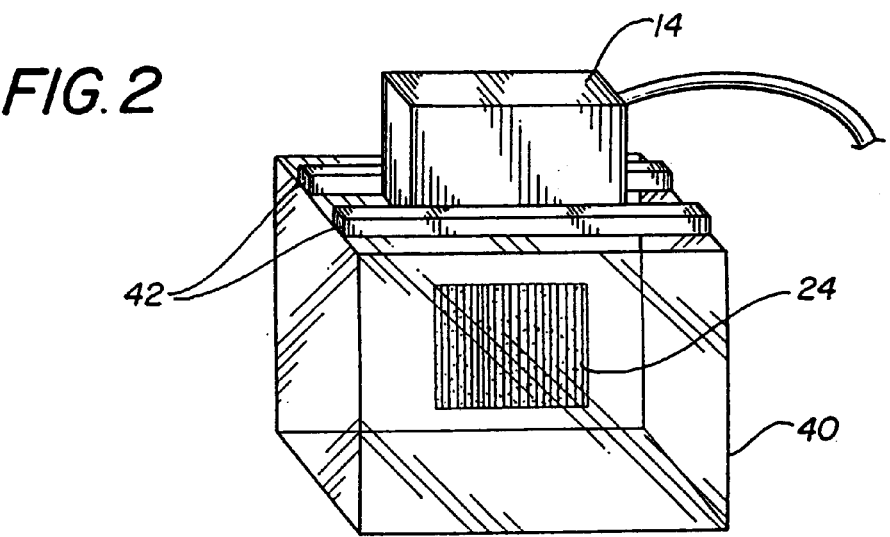
FIG. 2 is a diagram showing a thin film phantom suspended in a tissue mimicking propagation media below the transducer of an ultrasonic imaging system; the phantom being provided in accordance with an embodiment of the invention.

Referring to FIG. 2, there is shown a block 40 containing tissue mimicking material (the propagating medium) in which the thin film phantom is located. Alignment guides 42 on top of the block which themselves are aligned with the plane of the phantom, enable alignment of the transducer 14 of the ultrasound imaging system. The imaging system was evaluated by an imaging system processor and analyzing system such as described in connection with FIG. 1.

Figure 3:
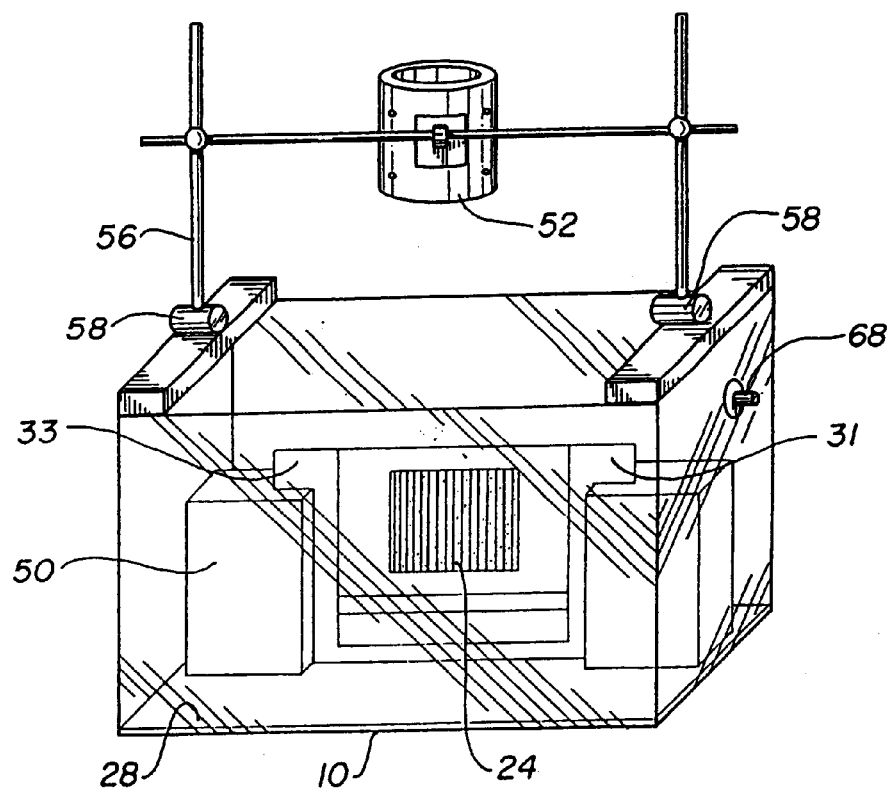
FIG. 3 is a perspective view illustrating schematically the apparatus of a system embodying the invention which utilizes replaceable and vibratable thin-film phantoms.

Referring to FIG. 3, the tank 10 containing the propagating medium (e.g. water) holds the phantom frame 33 in notches in a phantom insert guide bracket 50 which facilitates interchange of phantoms 24 having different patterns. The transducer 14 (is not shown) but is arranged in a transducer holder 52 which is mounted on a two-sided stand 56 with joints which provide for universal adjustability and alignment of the transducer. The stand 56 may also be tilted about journals 58 and translated along tracks 59 to adjust the offset and angle of the transducer beam with respect to the plane of the phantom 24.

An electrical contact 68 may be provided in order to bring leads through the tank to the phantom for purposes of piezoelectrically displacing the phantom when Doppler measurements are desired as will be explained more fully hereinafter in connection with FIGS. 6 and 7.

Figure 4A:
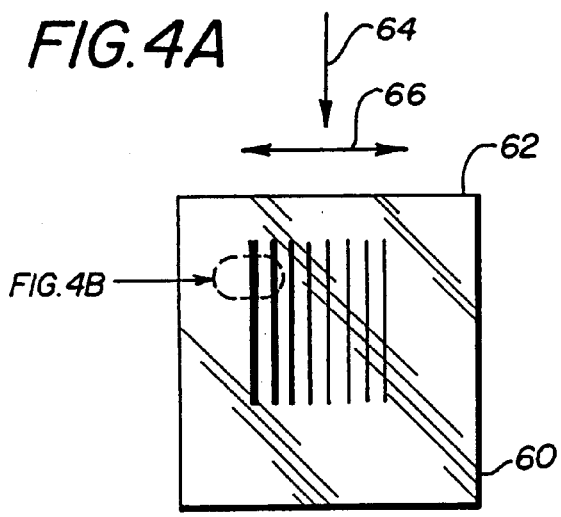
FIGS. 4A through O are front, top and sectional views through different thin-film phantoms which show regions of precisely controlled sub-resolvable scatterers which may be of different density, number of layers, materials, etc. all in accordance with different embodiments of the invention.
Figure 4B:
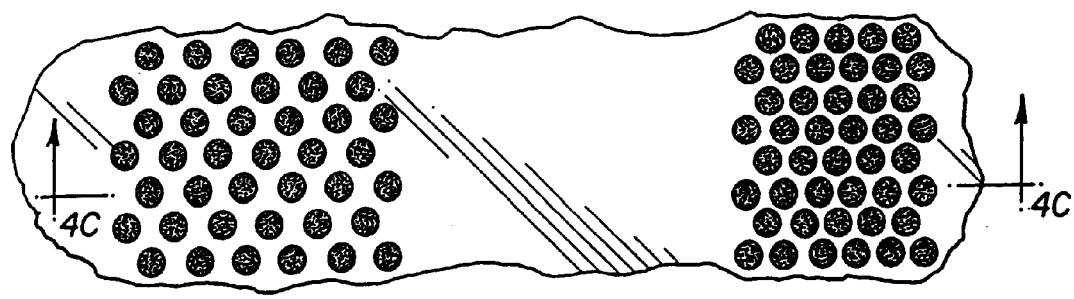
Figure 4C:
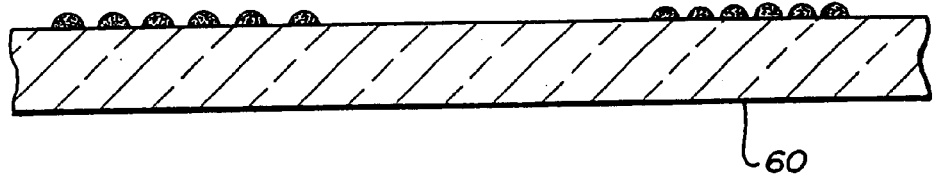

FIG. 4A shows the exemplary pattern of parallel equally spaced lines on a thin film or sheet 60 which provides an exemplary phantom 62. FIGS. 4B and C are enlarged fragmentary top and sectional views of the area within the dashed lines on FIG. 4A. The thin film 60 is the substrate on which dots of toner are printed to provide subresolvable scatterers in regions of subresolvable scatterers constituting the two left hand lines of the pattern in FIG. 4A. The subresolvable scatterers (dots) are deposited on the substrate with precisely specified distribution of dots so as to define desired echogenicity when the sheet is insonated by a transducer which projects a beam in the direction of an arrow 64 to insonate the phantom 62. The distribution of dots may be regularly spaced, or may be more unstructured as typically specified by the blue noise mask. The beam may scan laterally across the edge of the phantom in the direction indicated by the double-headed arrow 66.

Figure 4D:
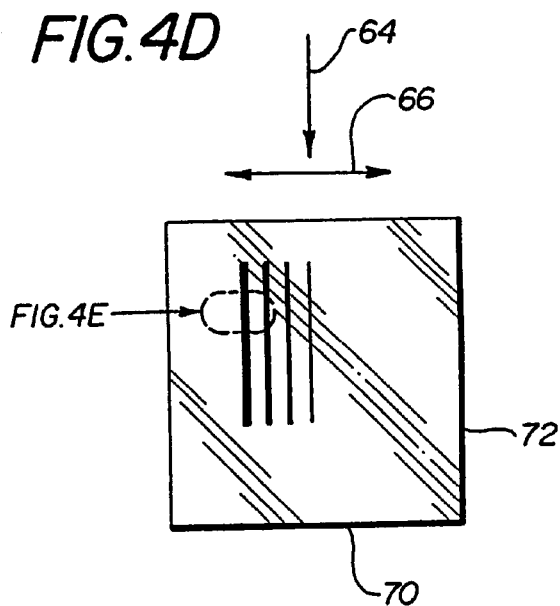
Figure 4E:
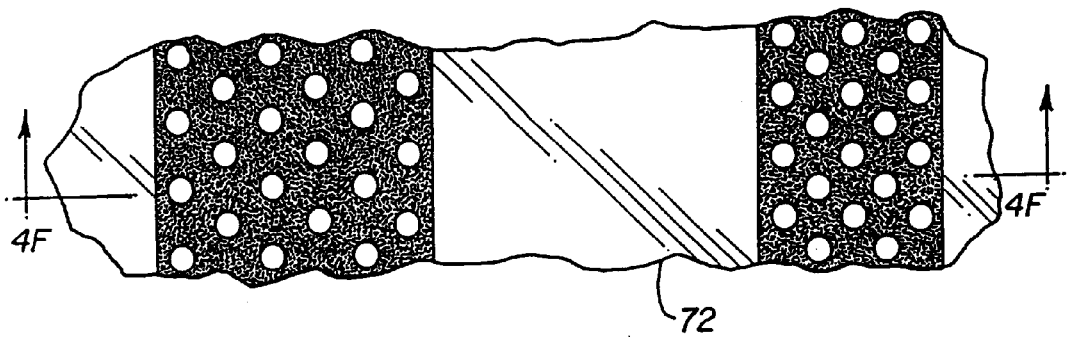
Figure 4F:
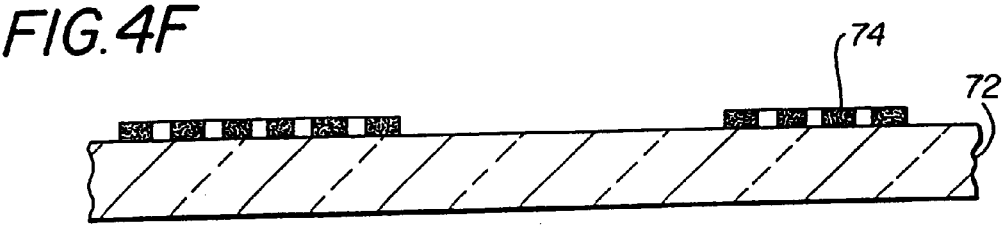

In FIG. 4D, a front view of another phantom 70 having parallel linear regions forming the pattern on the thin film sheet or substrate 72 is produced by etching a subresolvable voids in a layer 74 of material with a significant acoustic impedance difference from the material of the substrate 72 and the tissue mimicking material (water) which may fill the tank (10—FIG. 1). The layer 74 is etched away completely to form the lines of the pattern. The scattering is produced by etching of subresolvable voids in the layers which form the lines of the pattern. The voids are in a precisely specified and controlled distribution within the regions. The top view of FIG. 4E shows the voids as does the sectional view of FIG. 4F.

Figure 4G:
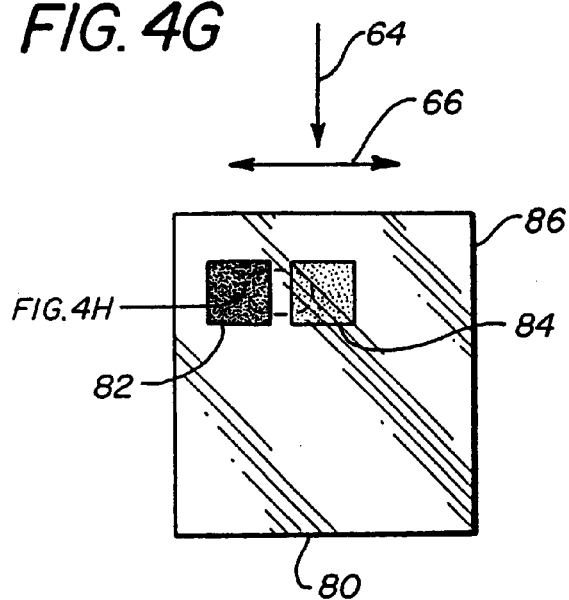
Figure 4H:
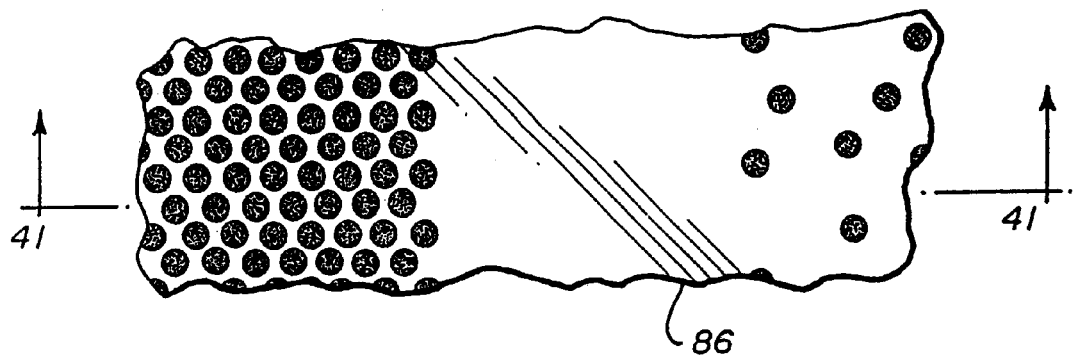
Figure 4I:
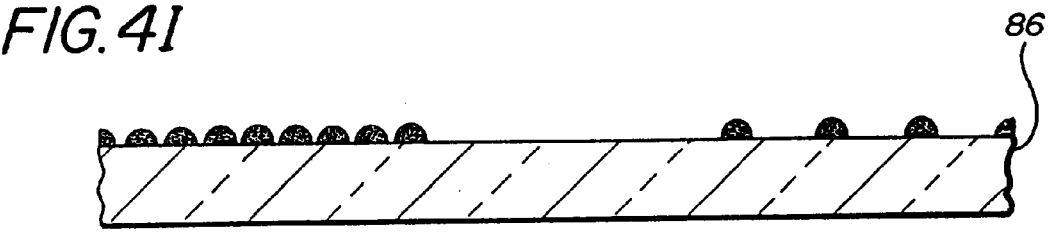

FIG. 4G shows a phantom 80 with regions 82 and 84 on the thin film (sheet) substrate 86. These regions have subresolvable scatterers which are deposited as by laser printing in the form of dots with precisely defined distributions and spatial density sufficient to produce precisely determined different gray scale levels on the ultrasound imaging system display. The distributions are more apparent from the enlarged top view of FIG. 4H and the sectional view of FIG. 4I.

Figure 4J:
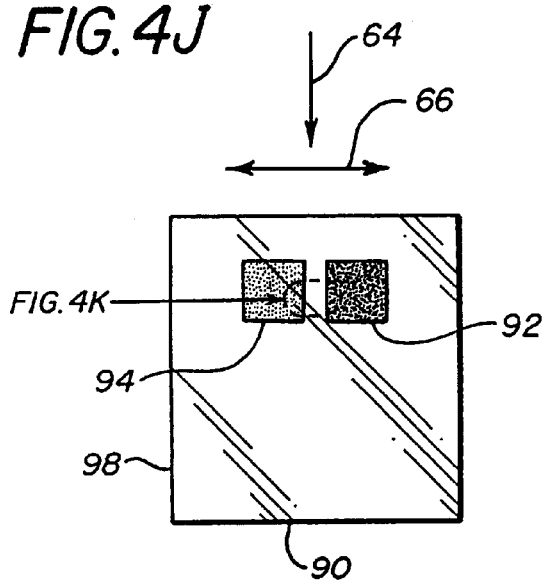
Figure 4K:
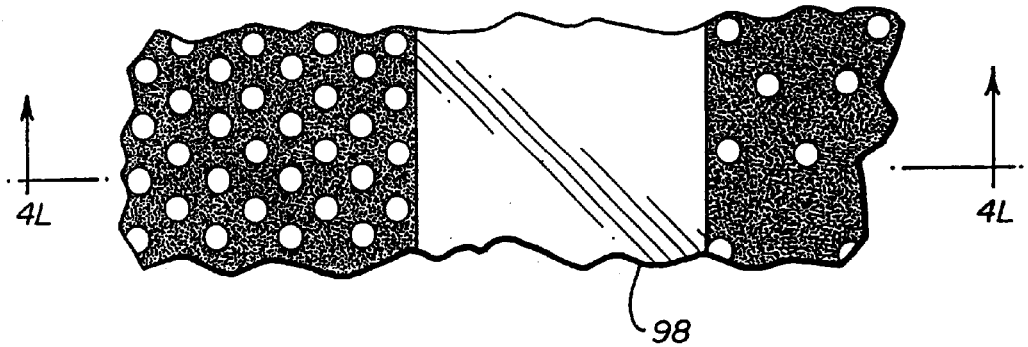
Figure 4L:
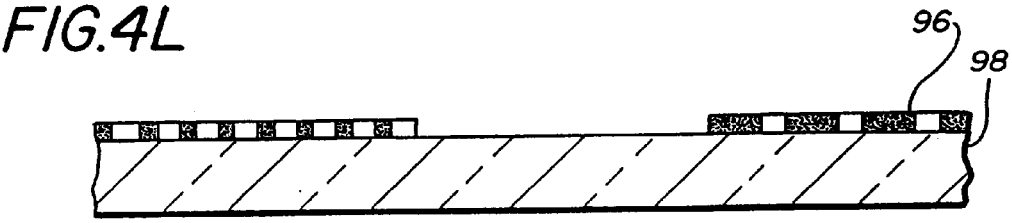

FIG. 4J is another phantom 90 with regions 92 and 94 which produce significantly different gray scale levels on the ultrasound imaging system display. These regions are formed by etching of a layer 96 of material with a significantly different acoustic impedance from the tissue mimicking material and the material of the thin film sheet 98 on which the patterns are provided by etching the layers to produce distributions of subresolvable voids. The enlarged top view of FIG. 4K and sectional view of FIG. 4L are of the area within the dashed line in FIG. 4J.

Figure 4M:
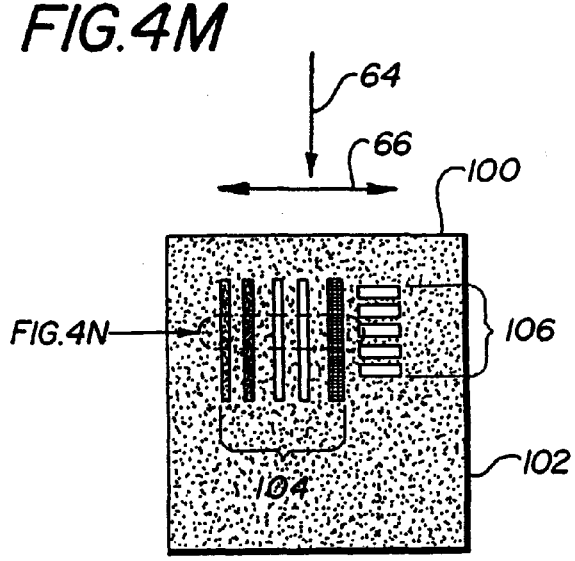
Figure 4N:
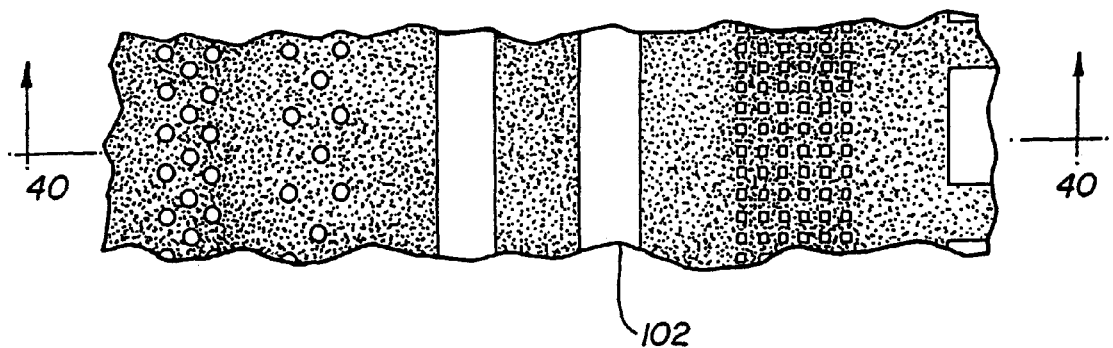
Figure 4O:
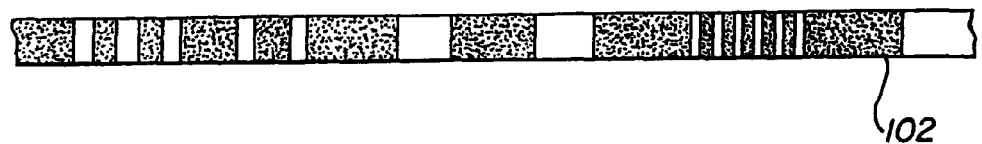

FIG. 4M shows a phantom 100 where the thin film (sheet) which provides the substrate 102 is a thin film of a material with acoustic impedance significantly different from the tissue mimicking material and may, for example, be nickel. The phantom 100 has several linear regions 104 and block shaped regions 106 which have precisely placed voids and occlusions such that controlled scattering is produced at the interface between the thin film 102 and the tissue mimicking material (the water in the tank 10—FIG. 1, for example). The top view of FIG. 4N and the sectional view of FIG. 4O are within the dashed lines on FIG. 4M.

Figure 5A:
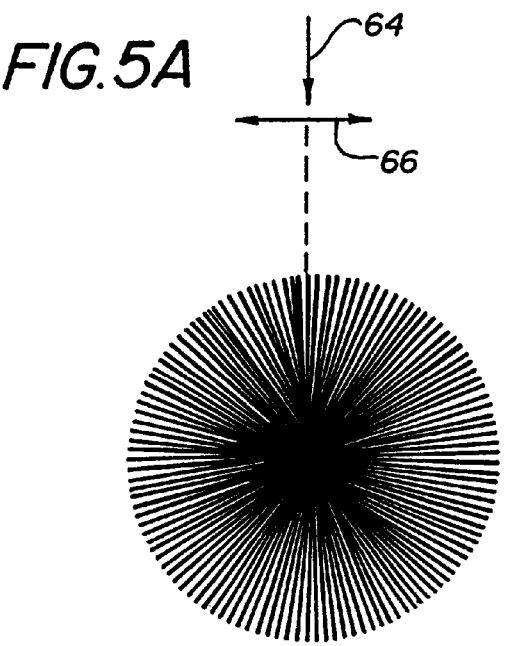
FIGS. 5A through L are diagrams of different thin-film phantoms which have different patterns of regions of sub resolvable scatterers in accordance with the invention.

Referring to FIG. 5A, there is shown a pattern of radially disposed regions which forms a star. Such pattern may be used for simultaneously testing axial and lateral resolution, MTF and spatial aliasing imaging science characteristics of the ultrasound imaging system.

Figure 5B:
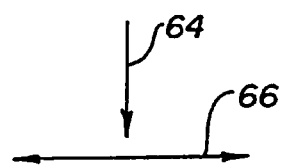
Figure 5B:
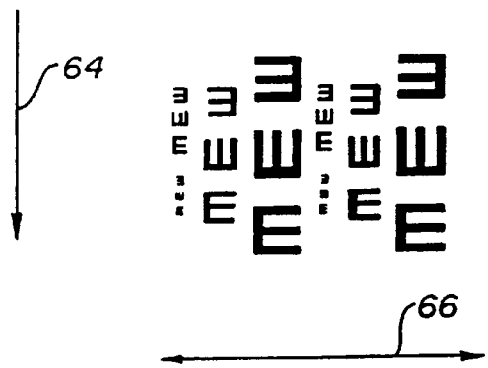

FIG. 5B is a pattern of regions in the form of lateral letter Es. The lateral E pattern primarily characterizes lateral performance at varying depths in the direction of propagation of the ultrasonic beam 64.

Figure 5C:
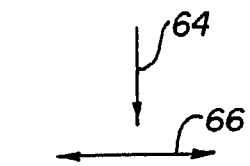
Figure 5C:
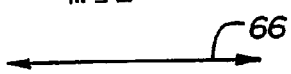

FIG. 5C is a pattern of axial Es. This axial E pattern characterizes axial performance over the lateral extent which the beam 64 scans in the direction 66.

Figure 5D:
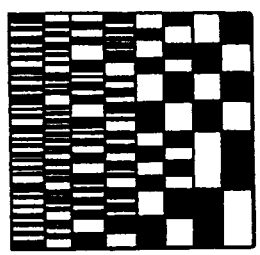
Figure 5E:
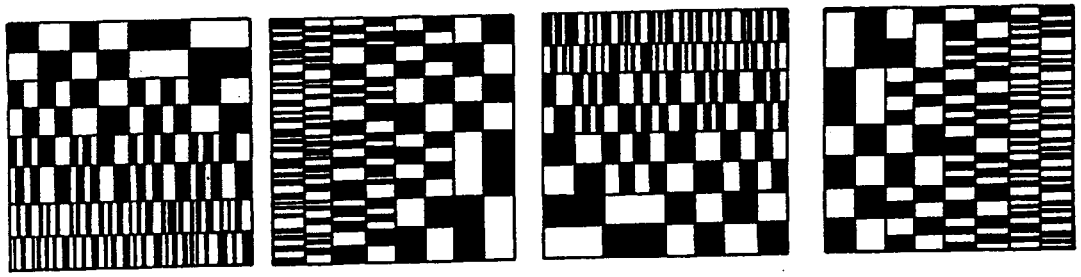

FIGS. 5D and E are single and multiple checkerboard patterns, respectively. These patterns may be used with the transducer producing the beam pattern 64 projecting in the axial direction as shown or laterally from the left or right or even from the bottom thus providing four orthogonally rotated images which can be observed side by side for simultaneous characterization of aliasing, resolution and frequency response.

Figure 5F:
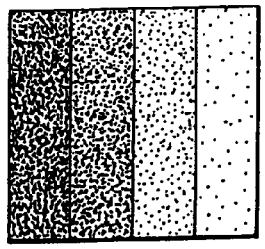

FIG. 5F shows a pattern of four regions constituting blue noise mask (BNM) halftone patterns at 13% and 37% threshold and inverse 13 and 37% thresholds. The blue noise masks may be oriented vertically (in the axial direction) as shown or may be rotated 90° either to the right or to the left. The changing density with depth allows characterization of TGC (time gain compensation) performance of the ultrasonic imaging system.

Figure 5G:
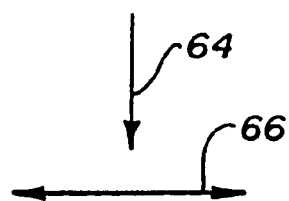
Figure 5G:
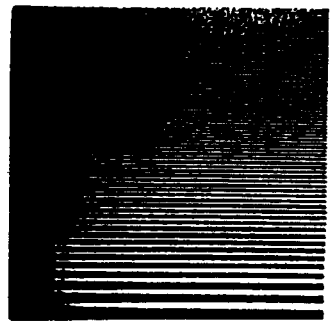

FIG. 5G shows an axial "chirp" pattern with a sinusoidal variation of scatterer density at increasing spatial frequency. The pattern may be rotated 180° so as to decrease the spatial frequency of the chirp with increasing depth.

Figure 5H:
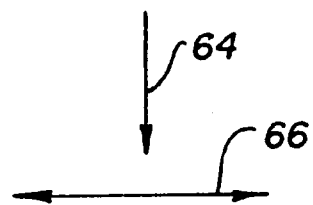
Figure 5H:
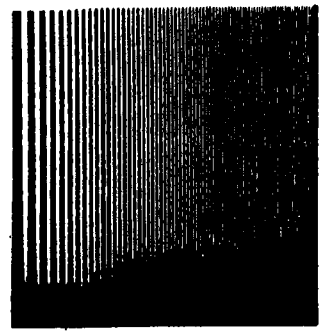

FIG. 5H shows a lateral "chirp" pattern with sinusoidal variation of scatterer density at increasing spatial frequency. It is shown oriented with increasing contrast from top to bottom (with axial depth). The contrast variation within a given cycle is due to the change in subresolvable scatterer density in the pattern.

Figure 5I:
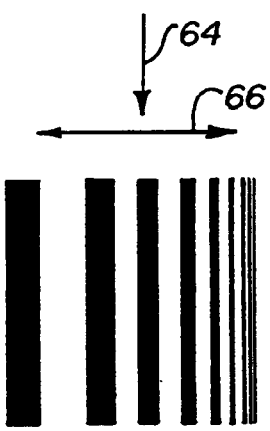
Figure 5J:
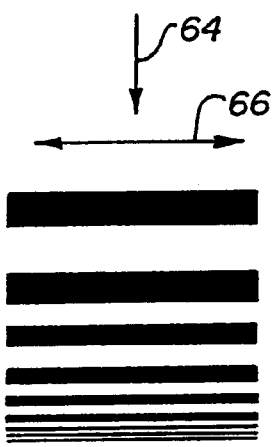
Figure 5K:
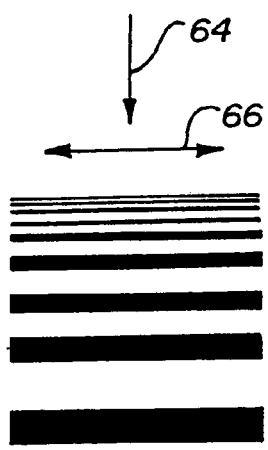

FIGS. 5I, J and K show different line pair chirp patterns for lateral and axial chirps. FIG. 5J shows the axial chirp with spatial frequency increase with depth, while FIG. 5K shows the axial chirp with decreasing spatial frequency with depth.

Figure 5L:
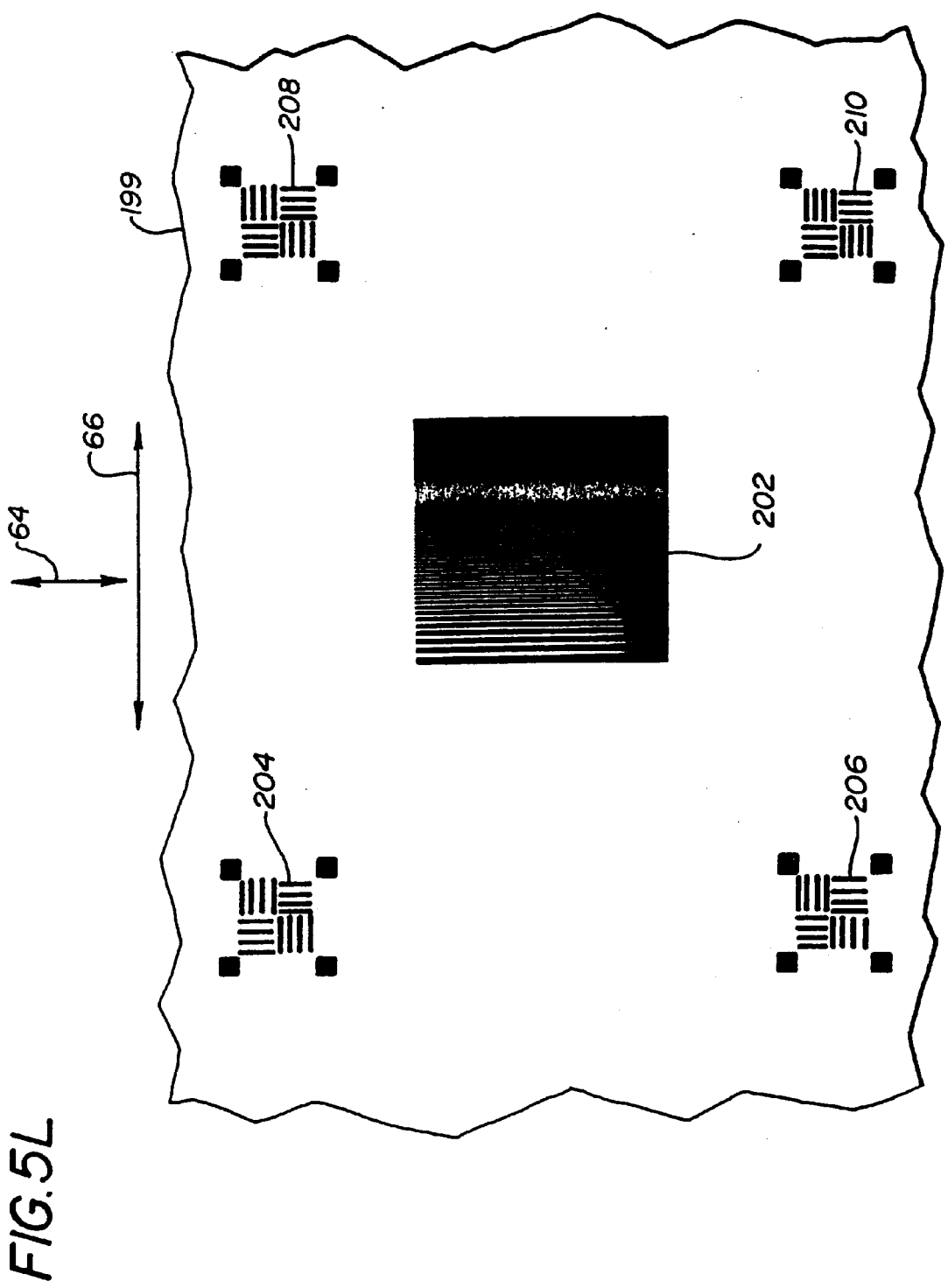

Referring to FIG. 5L there is shown a phantom 199 line pair "chirp" pattern 202 with secondary square and line patterns 204–210 located adjacent to the pattern 202 for alignment purposes. If transducer is properly aligned with plane of primary pattern 202 with time-gain compensation in the ultrasonic imaging system, the four secondary patterns 204–210 are displayed with similar intensity on the displayed image. Thus indicating that the phantom 198 is aligned with the beam 64 as it scans in the lateral directions 166.

Figure 6:
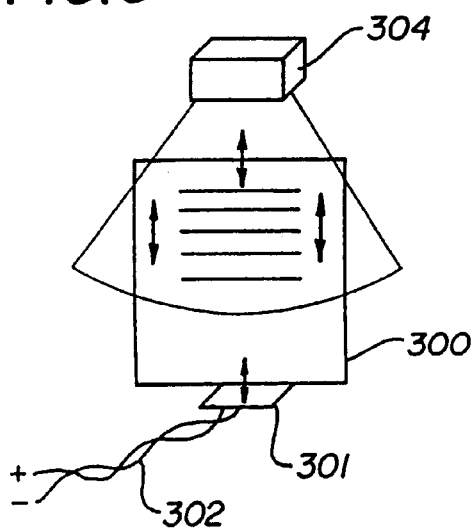
FIG. 6 is a schematic diagram illustrating a system whereby a thin-film phantom in accordance with the invention may be precisely displaced to provide Doppler information.
Figure 7:
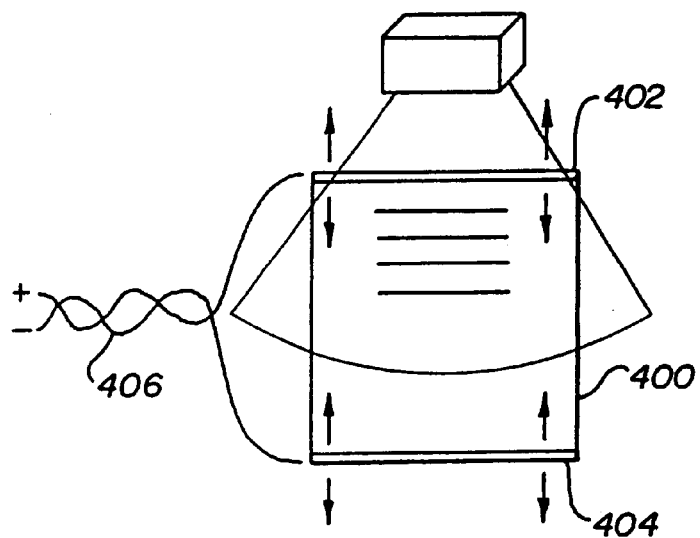
FIG. 7 is a schematic diagram similar to FIG. 6 of a system in accordance with the invention using a precisely displaceable thin film phantom having a piezoelectric film substrate.

FIGS. 6 and 7 show, schematically, how a thin film target may be precisely displaced as by being vibrated. The thin film target is a phantom 300 in FIG. 6 to which is attached a film of piezoelectric material such as PVDF 301 to which electrodes are connected by leads 302. The transducer 304 insonates the phantom 300 and obtains an image containing Doppler (velocity) information (the rate of vibration of the phantom 300).

Figure 8:
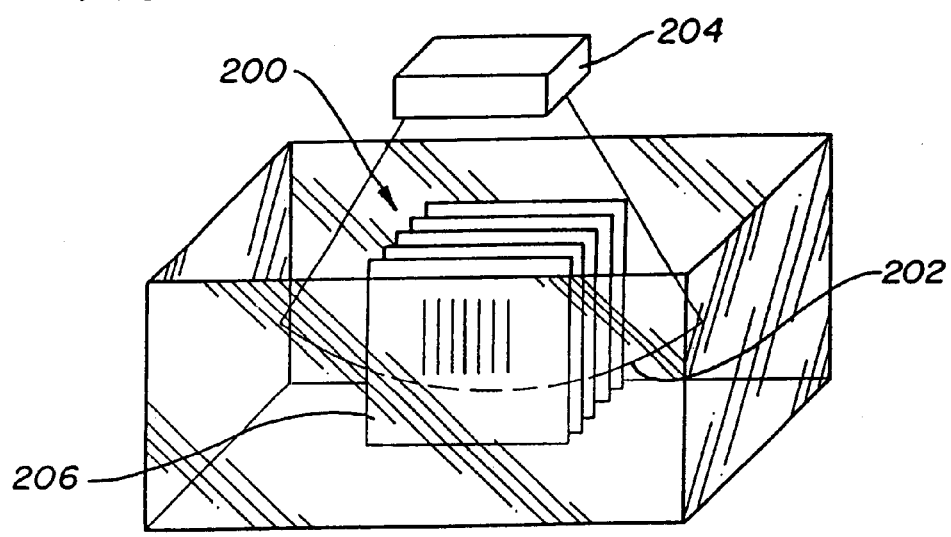
FIG. 8 is a schematic diagram of a system in accordance with the invention utilizing a multiplicity of thin-film phantoms.

FIG. 8 schematically illustrates a multiplicity of thin film targets or phantoms 200 in a tank submerged in a propagating medium (e.g., water). The interrogating ultrasonic beam scans laterally from left to right and axially along the planes of the sheets. The transducer 204 may be moved in a direction perpendicular to the lateral direction of the sweep of the beam from the transducer indicated by the arc 202 so as to allow measurement of beam thickness in the elevation axis and its effects on the displayed image.

A phantom 400 as shown in FIG. 7, is a sheet of piezoelectric film, such as PVDF with electrodes 402 and 404 deposited along its edges. A varying electrostatic field is applied across the phantom 400 via leads 406 and displaces the sheet with its pattern (the phantom—400) in the axial direction. Such displacement may have a sinusoidal vibration and provide an image containing Doppler (velocity) information.

With both the embodiments of FIGS. 6 and 7, the doppler performance of the ultrasonic imaging system may be tested including continuous wave Doppler (velocity) pulsed wave Doppler (velocity) and color Doppler (velocity) imaging modes.

Now consider the present invention which enhances and applies the invention to the testing of CT and MRI imaging systems. In both MRI and CT, body imaging cross-sectional thickness between 5 mm and 1 mm are common, and in-plane resolution of nearly one millimeter can be achieved in routine whole body imaging. Thus, subresolvable digital scatterers, that is regions of significantly different magnetic resonance and x-ray properties dimension cannot be individually resolved by conventional body imaging MRI and CT scanners. However, regions comprised of precise number and precisely deposited scatterers on a thin film can be resolved by MRI and CT scanners. In one embodiment, FIGS. 4A–4C and FIGS. 4G–4I, a thin film and any surrounding materials are selected to possess magnetic resonance and x-ray properties similar to those of human soft tissues. The deposited material is chosen to have significantly different magnetic resonance and/or x-ray absorption properties. Examples include paramagnetic materials such as gadolinium, plastics, lead, iron, and iodine-rich materials. (See, for example Frayne, et al. "A geometrically accurate vascular phantom . . . ", Med Phys 20(s), pp. 415–425, 1993). Half toning methods can be employed to vary the number of digital scatterers per surface area on selected regions of the thin film, so as to produce regions of preselected contrast with respect to the surrounding medium. The regions can be arranged so as to produce useful image science test patterns such as line pairs, chirps, wheels, and graded contrast regions.

In the MRI and CT imaging, the thin film plane is oriented perpendicular to the slice thickness (z-axis) direction of the MRI or CT scanners, such that the entire thin film plane is imaged. Note that a plurality of parallel planes with the same or with different patterns could be easily constructed so as to produce a slice thickness phantom or, in the limit as the parallel thin films are spaced at very close separation, a volumetric 3-D phantom is possible with precisely controlled volumetric magnetic resonance and x-ray properties.

As shown in FIGS. 4D–4F and FIGS. 4J–4O, voids are produced in a deposited layer that is chosen to have significantly different magnetic resonance and/or x-ray properties from the surrounding medium. In areas with a large number of voids, the image intensity will approach that of the surrounding material. However, in areas with very few voids, the image intensity will be more influenced by the properties of the deposited layer. Using halftone techniques to precisely vary the density of the voids within the defined regions, patterns can be established with precisely controlled contrast when imaged by MRI and CT scanners.

Figure 9:
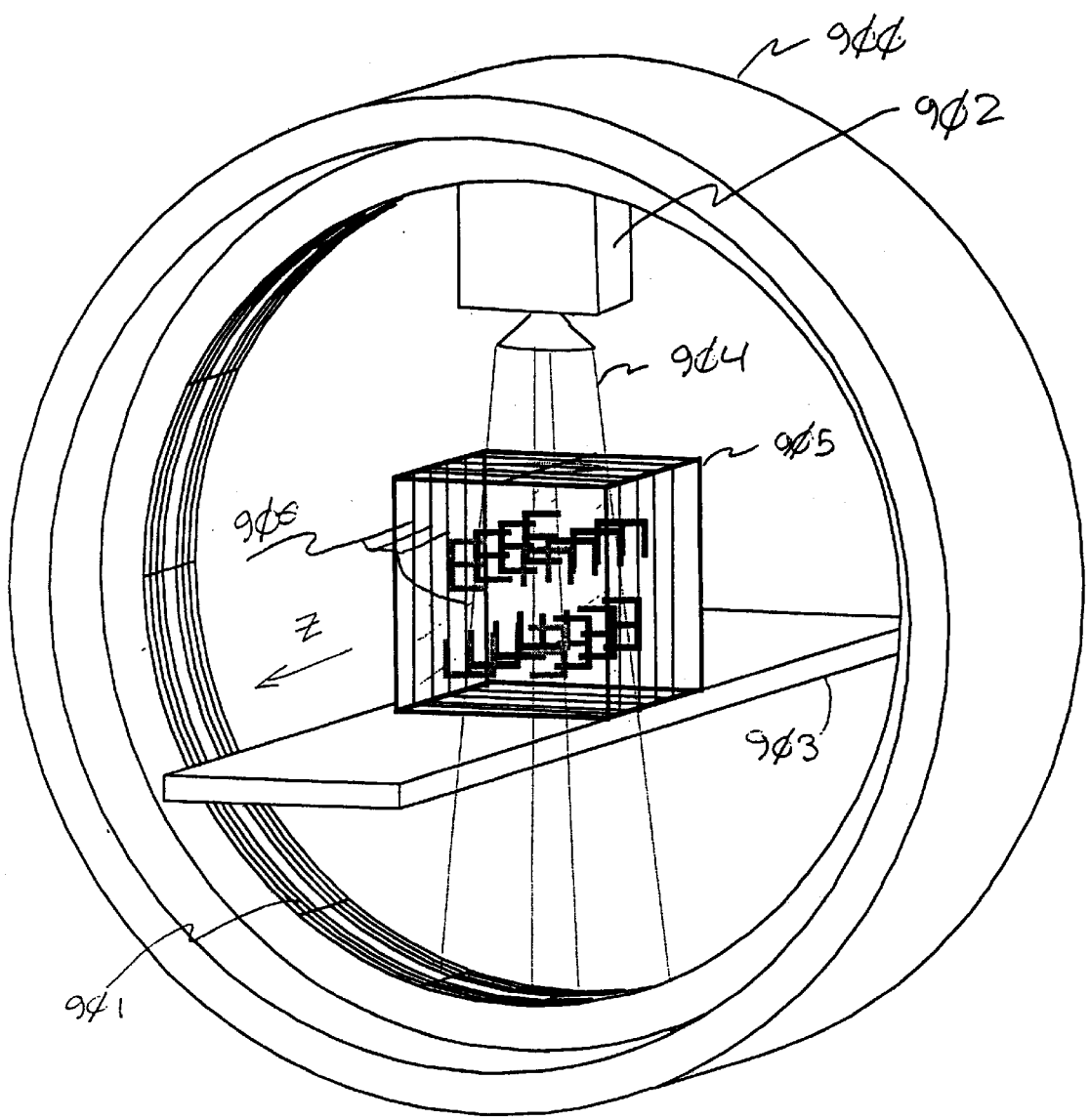
FIG. 9 is a perspective view of the use of a phantom according to the invention with a computerized tomography x-ray (CT X-ray) system where the invention is placed on a platform normally occupied by an object to be imaged.

FIG. 9 shows the x-ray phantom 906 in a radiolucent mounting fixture 905 containing the phantom, which is in the form of, for example, five (5) thin films 906 oriented in parallel planes. The phantom 906 is placed on the patient table 903 so that the tin films are parallel to the major axis of X-ray beam 904 produced by a rotating X-ray tube assembly 902. The X-ray tube assembly 902 rotates along a circumferential track contained in a gantry 900 and is sensed by detectors 901 that are either fixed along the internal circumference of the gantry, but may rotate in synchrony diametrically opposite to the rotation direction of the X-ray tube assembly. The patterns ("E"s) placed on the thin film serve to attenuate the generated X-rays as they travel towards the detectors producing signals that are processed and utilized to generate an image.

Figure 10:
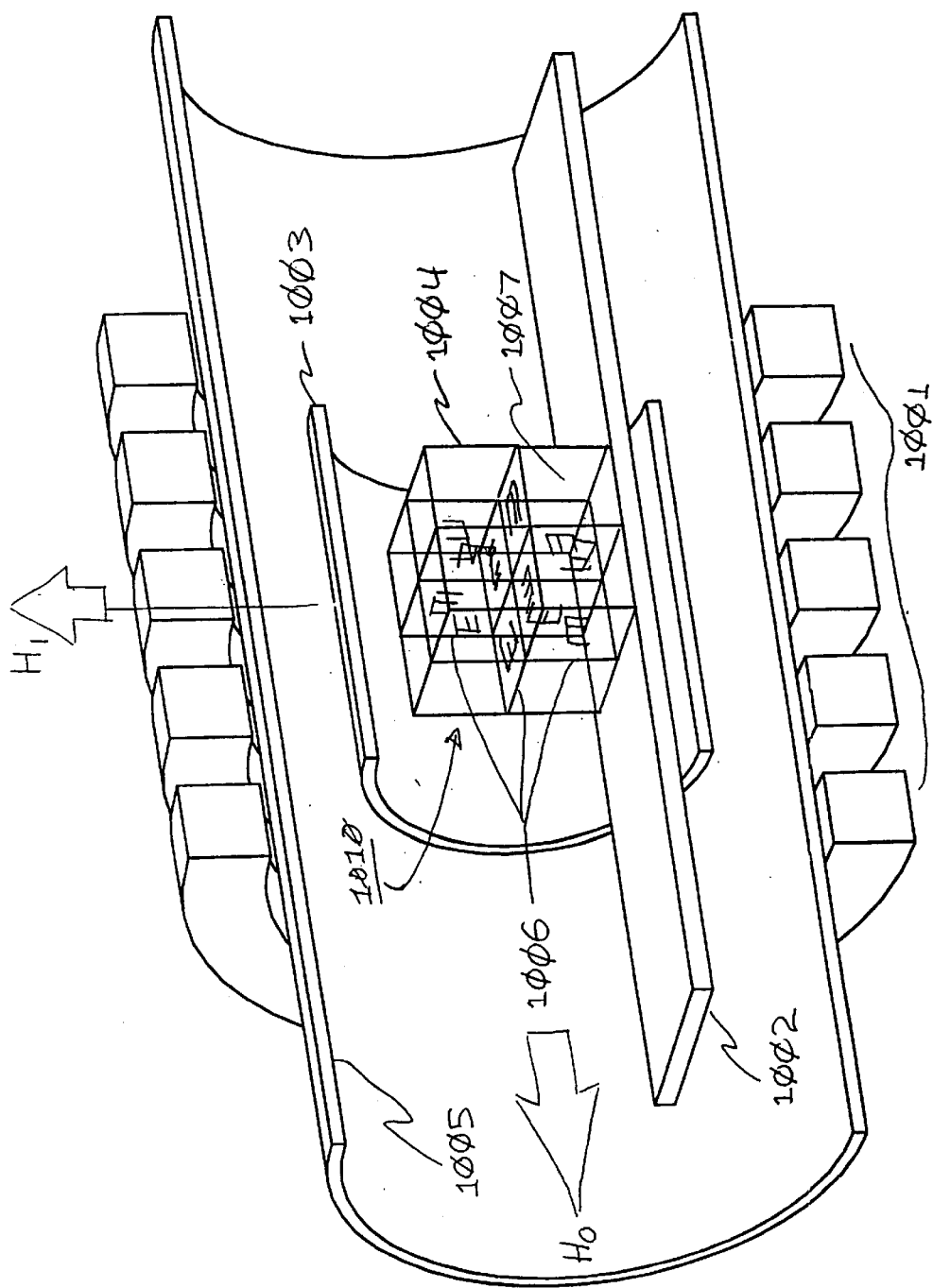
FIG. 10 is a perspective cut-away view of the use of a phantom according to the invention with a typical magnetic resonance imaging (MRI) system. The phantom is located in a position normally occupied by an object to be imaged. The thin films of the test object are oriented co-planar to three major axes of the imaging system.

FIG. 10 shows an MRI phantom 1010. A mounting fixture and container 1004 comprised of a non-ferromagnetic material and containing one or more thin films 1006 of the phantom 1010. The film is shown in planes which are perpendicular to each other, but may be in other relative orientations. In this case, the thin films 1006 are oriented along the three major axes of the magnetic resonance imaging system. The MRI system is primarily composed of (a) soledonial magnets 1001 to produce a homogeneous static magnetic field $H_0$, (b) a gradient coil system 1005 to produce a time and spatial varying imaging magnetic field, and (c) and RF coil system 1003 utilized to produce a magnetic field $H_1$ necessary to stimulate resonance phenomenon of the object being imaged. The same RF coil is used to measure the resultant signals. The phantom 110 is placed on the patient table 1002 normally occupied by the object to be imaged.

Figure 11:
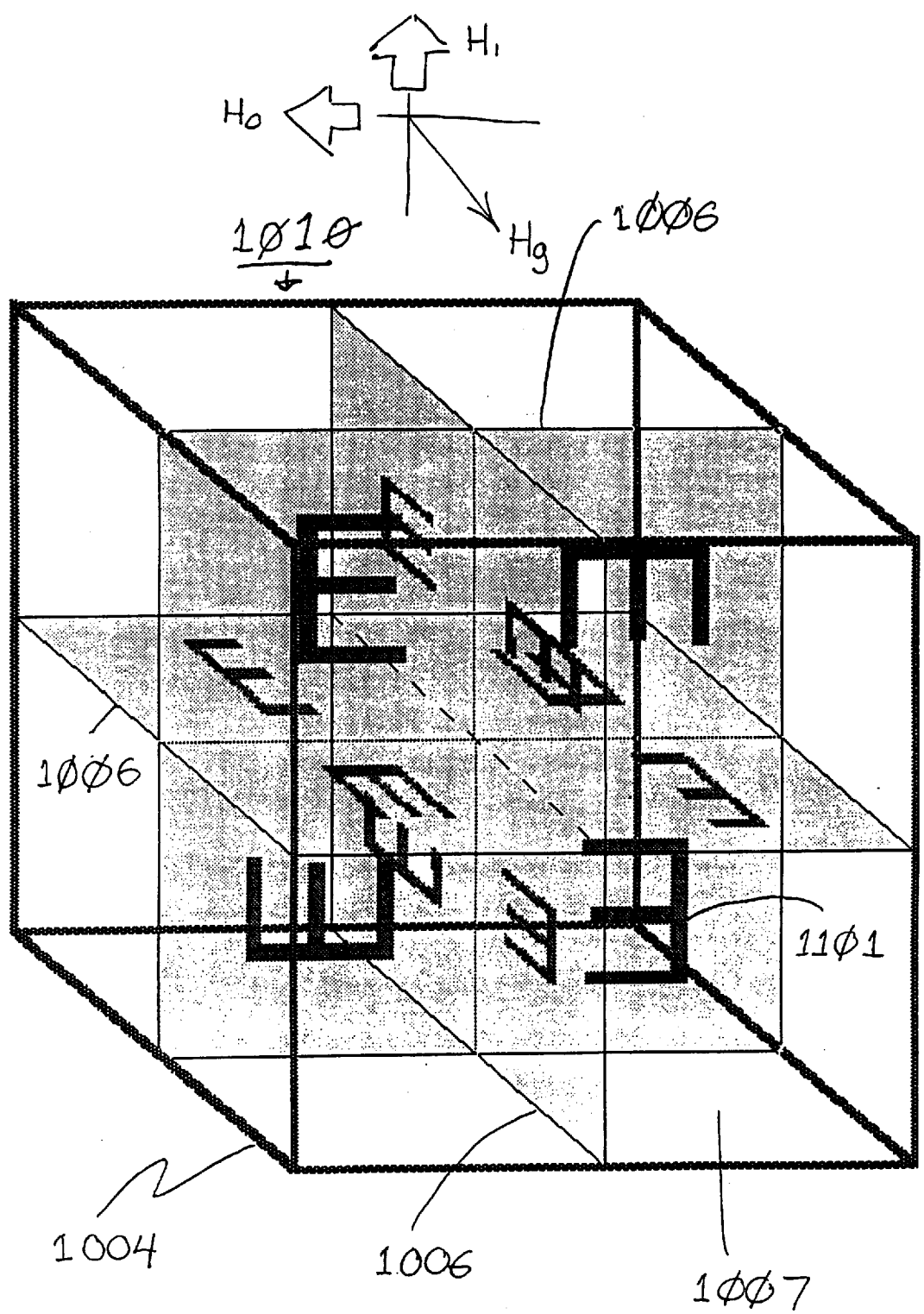
FIG. 11 is an enlarged perspective view of a phantom according to an embodiment of the invention utilized in the MRI system with indication of the major magnetic fields.

FIG. 11 is an enlarged perspective view of the phantom shown in FIG. 10, showing its relevant features with respect to the major magnetic axes $H_0$ and $H_1$ as well as an arbitrary gradient field $H_g$ necessary for image reconstruction. It should be noted that since an MRI is inherently a volume imaging modality capable of imaging arbitrarily oriented cross sections, that the thin films contained in the phantom 1010 may be oriented in an arbitrary manner as dictated by the evaluation parameters of interest. The patterns ("E"s) 1101 on the thin films may be comprised of various ferro, para, non or plain magnetic material or voids in such materials and may be immersed in various ferro, para, non or plain magnetic materials 1007 existing in a gaseous, liquid, gelatinous or solid state or in a vacuum void of any material. It should be noted that, especially for MRI, that the thin film may provide a pattern of varying magnetic characteristics in a variety of ways. For example: (1) the thin film may have deposited on it a pattern of material with magnetic character significantly different from that of the film and the volume surrounding the thin film; (2) the thin film itself may have significant magnetic characteristics relative to the pattern deposited on or etched in or to it (essentially a negative of type (1) above; (3) the thin film may have voids etched in to it and then be immersed in a media with significant magnetic characteristics. The interrogating electromagnetic fields then interact with the embedding media. In the plane of the thin film, the imaged pattern is disposed where the magnetic embedding media fills the voids in the thin film. Generally the patterns present a volume distribution of subresolvable magnetic or non-magnetic micro regions, called scatterers herein. CT planar and volume phantoms similarly have patterns presented by use of an embedding medium constituted of subresolvable scatterers of X-ray absorbing material such as an iodine containing solutions From the foregoing description, it will be apparent that there has been provided improved thin film phantoms and phantom systems. These phantom systems have regions of patterns in various forms and arrangements in addition to those described in the foregoing specification. Such other patterns and regions as well as variations and modifications in the phantoms themselves, will undoubtedly suggest themselves to those skilled in the art. Accordingly, the foregoing specification and description should be taken as illustrative and not in a limiting sense.

What is claimed is:

1. A method of testing a magnetic resonance imaging system which forms images of objects with electro-magnetic energy processed to produce tomographic slices of a body to be imaged, said method comprising:

providing a pattern of resolvable regions of precisely spaced, individually sub-resolvable scatterers on a planar medium;

forming an image of said pattern in said system so as to resolve said resolvable regions; and analyzing said image to evaluate the performance of said system.

2. The method according to claim 1 wherein said analyzing step is carried out to evaluate performance as manifested by characteristics selected from the group consisting of distortion, aberrations, imaging artifacts, spatial frequency response, modulation transfer function (MTF), aliasing, and resolution limits.

3. The method according to claim 1 wherein said analyzing step is carried out to calibrate said MRI imaging system.

4. The method according to claim 1 wherein said sub-resolvable scatterers are digital scanners, and wherein said regions are the only areas of said medium which constitute significant different magnetic resonance properties.

5. The method according to claim 1 wherein said step of providing said pattern is carried out to produce said regions with precisely controlled magnetic resonance properties.

6. The method according to claim 5 wherein said precisely controlled scattering properties are obtained by selecting sizes and distribution of said sub-resolvable scatterers in said regions.

7. The method according to claim 5 wherein said regions of precisely controlled scattering properties are formed by a step selected from the group consisting of electrostatic printing, etching, photo-lithographic printing, sputtering and vacuum deposition, with material having magnetic resonance properties detectably different from the material of said planar medium.

8. The method according to claim 5 wherein said regions of precisely controlled scattering properties are formed by producing half-tones in said regions thereby providing an image having selectable grey scale contrast.

9. The method according to claim 5 wherein said precisely controlled scattering properties are obtained by selecting at least one characteristic of said regions from the group consisting of the magnetic properties, the proton density, the relaxation constants, the thickness of said scatterers, materials of said medium having selected magnetic resonance characteristics.

10. The method according to claim 8 wherein the half-tones have spatially varying densities.

11. The method according to claim 8 wherein the half-tones comprise blue noise masks.

12. The method according to claim 1 wherein said planar medium is a thin film or sheet substrate on which said pattern is deposited.

13. The method according to claim 1 wherein said medium consists of tissue mimicking material.

14. The method according to claim 1 wherein said providing step includes the step of maintaining said substrate in a plane oriented generally perpendicular to the slice thickness axis of the scanner.

15. The method according to claim 1 wherein information representing said image is transmitted over a communications link to a receiving station, and said analyzing step is carried out at said receiving station thereby enabling MRI systems operative via teleradiography links to be evaluated in said systems.

16. The method according to claim 1 wherein said pattern providing step is carried out to provide a second pattern located adjacent to said pattern of regions of sub-resolvable scatterers and further comprising the step of aligning said beam with said medium utilizing said second pattern.

17. The method according to claim 1 further comprising the step of arranging a plurality of planar mediums having patterns provided by said pattern providing step in side by side relationship with the planes of said mediums oriented perpendicular to the slice selection axis of the MRI scanner.

18. The method according to claim 1 wherein said resolvable regions comprise a plurality of resolvable lines formed of said individually sub-resolvable scatterers.

19. The method according to claim 18 wherein said plurality of resolvable lines are radially arranged.

20. The method according to claim 18 wherein said plurality of resolvable lines are parallel.

21. The method according to claim 20 wherein said plurality of resolvable lines have different thicknesses.

22. The method according to claim 1 wherein said step of analyzing comprises determining a modulation transfer function in an imaging chain in the system.

23. The method according to claim 1 wherein said step of analyzing comprises determining a spatial frequency response in an imaging chain in the system.

24. The method according to claim 1 wherein said step of providing comprises applying the scatterers onto the medium through a xerographic process.

25. A phantom for testing magnetic resonance imaging systems, the phantom comprising:

a planar medium having a surface; and a plurality of individually subresolvable scatterers having preselected magnetic resonance properties precisely located in a pattern of resolvable regions on said surface of said medium.

26. The phantom according to claim 25 wherein-said regions possess magnetic resonance properties that are substantially different from said medium surrounding said region.

27. The phantom according to claim 25 wherein said scatterers are sized and distributed such that said regions have precisely controlled magnetic resonance properties.

28. The phantom according to claim 25 wherein the areas of said regions provide said precisely controlled magnetic resonance properties.

29. The phantom according to claim 27 wherein said scatterers are sized and distributed to produce half-tones in said regions.

30. The phantom according to claim 29 wherein the half-tones have spatially varying densities.

31. The phantom according to claim 23 wherein the half-tones comprise blue noise masks.

32. The phantom according to claim 25 wherein said planar medium is a thin film or sheet substrate on which said pattern is disposed.

33. The phantom according to claim 25 wherein said planar medium provides a substrate which consists of tissue mimicking material.

34. The phantom according to claim 25 further comprising a plurality of planar mediums including said planar medium each having patterns in side-by-side relationship and with the planes of said mediums oriented in an axial direction of the slice thickness axis of said scanner.

35. The phantom according to claim 25 wherein said resolvable regions comprise a plurality of resolvable lines formed of said individually sub-resolvable scatterers.

36. The phantom according to claim 35 wherein said plurality of resolvable lines are radially arranged.

37. The phantom according to claim 35 wherein said plurality of resolvable lines are parallel.

38. The phantom according to claim 37 wherein said plurality of resolvable lines have different thicknesses.

39. A method of testing CT imaging systems using a beam of x-ray energy produced by the CT imaging system, said method comprising the steps of providing a pattern of regions of precisely spaced sub-resolvable scatterers of x-ray absorbing material on a planar medium, and analyzing an image formed by said pattern to evaluate the performance of said systems.

40. The method according to claim 39 wherein said analyzing step is carried out to evaluate performance as manifested by characteristics selected from the group consisting of distortion, aberrations, imaging artifacts, spatial frequency response, modulation transfer function (MTF), aliasing, and resolution limits.

41. The method according to claim 39 wherein said analyzing step is carried out to calibrate said CT imaging system.

42. The method according to claim 39 wherein said subresolvable scatterers are digital scatterers and regions are the only areas of said medium which constitute significantly different x-ray absorption properties of resolvable size.

43. The method according to claim 39 wherein said step of providing said pattern is carried out to produce said regions with precisely controlled x-ray absorption properties.

44. The method according to claim 43 wherein said precisely controlled x-ray absorption properties are obtained by selecting sizes and distribution of said subresolvable scatterers in said regions.

45. The method according to claim 43 wherein said regions of precisely controlled x-ray absorption properties are formed by a step selected from the group consisting of electrostatically printing, etching, photo-lithographic printing, sputtering and vacuum deposition, with material having an x-ray absorption detectably different from the material of said planar medium.

46. The method according to claim 43 wherein said regions of precisely controlled x-ray absorption properties are formed by producing half-tones in said regions thereby providing an image having selectable grey scale contrast.

47. The method according to claim 43 wherein said providing step includes the step of maintaining said substrate in a plane oriented generally in the direction of propagation of said x-ray energy.

48. The method according to claim 43 wherein said precisely controlled x-ray absorption properties are obtained by selecting at least one characteristic of said regions from the group consisting of the density of said subresolvable scatterers, the number of subresolvable scatterers per unit area, the thickness of said scatterers in a direction transverse to said plane of the medium, the x-ray absorption of said scatterers, materials of said medium having selected x-ray propagating characteristics, selected numbers of layers of said subresolvable scatterers, and the size of particles forming said scatterers.

49. The method according to claim 39 wherein said planar medium is a thin film or sheet substrate on which said pattern is disposed.

50. The method according to claim 39 wherein said medium consists of tissue mimicking material.

51. The method according to claim 39 wherein information representing said image is transmitted over a communications link to a receiving station, and said analyzing step is carried out at said receiving station thereby enabling x-ray imaging systems operative via teleradiography links to be evaluated in said systems entirety.

52. The method according to claim 39 wherein said pattern providing step is carried out to provide a second pattern located adjacent to said pattern of regions of subresolvable scatterers and further comprising the step of aligning said x-rays with said medium utilizing said second pattern.

53. The method according to claim 39 further comprising the step of arranging a plurality of planar mediums having patterns provided by said pattern providing step in side by side relationship with the planes of said mediums oriented in a direction which is generally along the direction of propagation of said x-rays.

54. A phantom for testing a CT imaging systems comprising a planar medium on which x-ray energy from the CT imaging system is incident to having at least one pattern of subresolvable scatterers precisely located on a surface of said medium.

55. The phantom according to claim 54 wherein said scatterers possess x-ray absorption properties that are substantially different from said medium surrounding said scatterers.

56. The phantom according to claim 54 wherein said scatterers are sized and distributed and have precisely controlled x-ray absorption properties, and are of resolvable size.

57. The phantom according to claim 56 wherein the patterns also present precisely controlled x-ray absorption properties.

58. The phantom according to claim 54 wherein said planar medium is a thin film or sheet substrate on which said pattern is disposed.

59. The phantom according to claim 54 wherein said pattern is a chirp pattern of bars of said scatterers, which bars have progressively varying widths and spacings to enable evaluation of the MTF characteristic of said CT systems.

60. The phantom according to claim 54 further comprising a plurality of planar mediums, including said planar medium, having patterns in a side-by-side relationship and with the planes of said mediums oriented in an axial direction which is generally along the direction of the slice thickness axis of said scanner.

61. A method of testing an imaging system which forms images of objects with electro-magnetic energy, said method comprising:
   providing a pattern of resolvable regions of precisely spaced, individually sub-resolvable scatterers on a planar medium;
   forming an image of said pattern in said system so as to resolve said resolvable regions; and
   analyzing said image to evaluate the performance of said system.

62. A phantom for testing electromagnetic imaging systems, the phantom comprising:
   a planar medium having a surface; and
   a plurality of individually subresolvable scatterers having preselected magnetic resonance properties precisely located in a pattern of resolvable regions on said surface of said medium.

\* \* \* \* \*

UNITED STATES PATENT AND TRADEMARK OFFICE
CERTIFICATE OF CORRECTION

PATENT NO. : 6,720,766 B2 Page 1 of 1
DATED : April 13, 2004
INVENTOR(S) : Parker et al.

It is certified that error appears in the above-identified patent and that said Letters Patent is hereby corrected as shown below:

Column 1
Line 3, insert the following: -- This invention was made under a contract with the National Institute of Health of the United States Government under Grant No. CA44732. The government has certain rights in this invention. --

Signed and Sealed this

Eighth Day of June, 2004

JON W. DUDAS
*Acting Director of the United States Patent and Trademark Office*